United States Patent

Dupont et al.

[11] 4,031,055
[45] June 21, 1977

[54] METAL COMPOUND STABILIZED COATING COMPOSITIONS

[75] Inventors: John A. Dupont, Glenside; Walter Kooch, Feasterville; Joseph D. Scott, Philadelphia, all of Pa.

[73] Assignee: Rohm and Haas Company, Philadelphia, Pa.

[22] Filed: May 28, 1975

[21] Appl. No.: 581,592

Related U.S. Application Data

[63] Continuation-in-part of Ser. No. 139,877, May 3, 1971, abandoned.

[52] U.S. Cl. .................... 260/29.6 MM; 106/15 R; 260/29.6 MQ; 260/29.6 MN
[51] Int. Cl.² ................... C09D 3/74; C09D 3/80; C09D 5/14
[58] Field of Search ......... 260/29.6 MM, 29.6 MQ, 260/29.6 MN, 29.6 H, 29.6 TA, 45.8 SN; 106/15 AF; 424/270

[56] References Cited

UNITED STATES PATENTS

3,523,121   8/1970   Lewis et al. .................... 260/306.7

OTHER PUBLICATIONS

Rose et al., The Condensed Chemical Dictionary (Reinhold, N.Y.) p. 1035, 1966.

*Primary Examiner*—Lucille M. Phynes
*Attorney, Agent, or Firm*—George W. F. Simmons; William E. Lambert, III; Bernard J. Burns

[57] ABSTRACT

Coating compositions which contain a mildew controlling amount of an isothiazolone are stabilized against chemical decomposition of the isothiazolone by the addition of a metallic compound. Among the compounds which can be used are the acetates, carbonates, chlorides, bromides, nitrates, sulfates, phosphates, and oxides of cadmium, cobalt, copper, lead, manganese, mercury, nickel, silver and zinc.

14 Claims, No Drawings

METAL COMPOUND STABILIZED COATING COMPOSITIONS

This application is a continuation-in-part of the now abandoned U.S. Ser. No. 139,877 filed May 3, 1971.

This invention relates to isothiazolone-containing coating compositions, particularly paints, in which the isothiazolone is stabilized against chemical decomposition and from which coatings with improved mildew resistance are obtained.

Coating compositions, and particularly latex paints, are often formulated at relatively high pH to improve their mechanical stability, freeze-thaw stability, and dispersion stability. However, 3-isothiazolones, which have been found to be excellent mildewcides, can undergo chemical decomposition under basic aqueous conditions, thus decreasing their effectiveness in controlling mildew in the final coating. It has now been found that the chemical decomposition of the isothiazolone in these coating compositions can be effectively minimized by the addition of a suitable metallic compound to the compositions. Not only are the coating compositions stabilized against chemical decomposition, but coatings produced from them show improved mildew resistance.

According to the invention a coating composition which comprises a film-forming material, a solvent or carrier, and a mildew-controlling amount of an isothiazolone is stabilized against chemical decomposition of the isothiazolone by incorporating into the composition a stabilizing amount of metallic compound. Generally, the isothiazolone has the formula

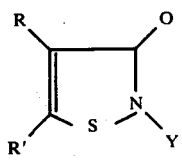

wherein Y is a hydrogen atom, a ($C_1$–$C_{18}$) alkyl group, a ($C_6$–$C_{10}$) aryl group, or a ($C_7$–$C_{10}$) aralkyl group, R is a hydrogen atom, a halogen atom, or a ($C_1$–$C_4$) alkyl group, R' is a hydrogen atom, a halogen atom, or a ($C_1$–$C_4$) alkyl group or, R and R' can be taken together to complete a benzene ring, optionally substituted with one or more halogen atoms, nitro groups, ($C_1$–$C_4$) alkyl groups, cyano groups, ($C_1$–$C_4$) alkoxy groups, or the like.

The definition of Y above includes both unsubstituted groups and groups substituted with one or more halogen atoms, ($C_1$–$C_4$) alkoxy groups, nitro groups, nitro groups, cyano groups, carboxy groups, carb ($C_1$–$C_4$) alkoxy groups, or the like.

A wide variety of metallic compounds can be used in the compositions of the invention, including salts of cadmium, cobalt, copper, lead, manganese, mercury, nickel, silver, or zinc. Among the compounds which can be used are the acetates, carbonates, chlorides, bromides, nitrates, sulfates, phosphates and oxides of these metals, as well as other similar metal compounds. In a preferred embodiment of the invention a zinc compound, usually zinc oxide, is used to stabilize the compositions.

The metallic compound can be added to the compositions of the invention in any concentration which will effect the desired stabilization of the 3-isothiazolone. Generally, the compound will be present at about 0.01 to about 100 pounds per 100 gallons of paint, preferably at about 1 to 50 pounds per 100 gallons of paint and most preferably at about 5 to 20 pounds per 100 gallons of paint.

The metallic compound is particularly effective in inhibiting chemical decomposition of isothiazolone-containing compositions which have been neutralized to a relatively high pH (greater than about 9.0) with ammonia or an organic amine, such as dimethylaminoethanol, triethylamine, morpholine, or the like. However, the compounds can be used to fortify against mildew attack any coating composition which contains a 3-isothiazolone, including oil-based paints, water-based paints formulated at any pH, lacquers, and other decorative or protective coating compositions.

The coating compositions of the invention contain at least one isothiazolone having Formula I. The method of preparation of these isothiazolones is disclosed in U.S. patent applications Ser. No. 841,548, filed on July 14, 1969, now abandoned, Ser. No. 836,660, filed on June 25, 1969, now U.S. Pat. No. 3,761,488 and Ser. No. 855,046, now abandoned, filed on Sept. 3, 1969, and in U.S. Pat. No. 3,517,022, of Miller et al., granted on June 23, 1970. Generally, the isothiazolones of Formula I in which R and R' do not form a benzene ring are prepared by the oxidative cyclization of a disulfide-amide having the formula

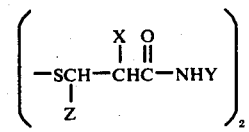

or, a mercapto-amide having the formula

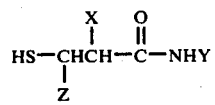

wherein X and Z are hydrogen or lower alkyl and Y is as defined above. The cyclization is accomplished by contacting the amide with a halogenating agent. Typical halogenating agents include chlorine, bromine, sulfuryl chloride, sulfuryl bromide, N-chlorosuccinimide, N-bromosuccinimide, and the like. Chlorine and sulfuryl chloride are the preferred halogenating agents. The benzisothiazolones of Formula I are prepared by the reaction of a primary mine with an o-halosulfenylbenzoyl halide or the intramolecular condensation of an o-halosulfenylbenzamide.

The concentration of isothiazolone which is added to the paint can vary over a wide range depending on such factors as the type of paint involved, the locality of application, and the type of surface on which the paint is applied. Generally, about 0.1 lb. to 20 lb. of isothiazolone per 100 gallons of paint will be effective. The preferred range of incorporation is about 0.5 lb. to 12 lb. of isothiazolone per 100 gallons of paint. Among the particularly useful isothiazolones are those in which Y in Formula I is an alkyl group, in which the alkyl group can have a branched- or straight-chain spatial configuration, including 2-butyl-3-isothiazolone, 2-hexyl-3-isothiazolone, 2-octyl-3-isothiazolone, 2- nonyl-3-isothiazolone, 2-decyl-3-isothiazolone, 2-dodecyl-3-isothiazolone and the like, and their 5-halo analogues.

In a preferred embodiment of the invention, the coating composition is an aqueous dispersion of a vinyl or acrylic emulsion polymer, such as those used in making water-based paints. Examples of such dispersions include homopolymers and copolymers, of: (1) vinyl esters of an aliphatic acid having 1 to 18 carbon atoms, especially vinyl acetate; (2) acrylic acid esters and methacrylic acid esters of an alcohol having 1 to 18 carbon atoms, especially methyl acrylate, ethyl acrylate, butyl acrylate, 2-ethylhexyl acrylate, methyl methacrylate, ethyl methacrylate and butyl methacrylate; and (3) mono- and di-ethylenically unsaturated hydrocarbons, such as ethylene, isobutylene, styrene, and aliphatic dienes, such as butadiene, isoprene, and chloroprene.

Poly(vinyl acetate) and copolymers of vinyl acetate with one or more of the following monomers: vinyl versatate or other vinyl esters of fatty acids having 3 to 18 carbon atoms, vinyl chloride, vinylidene chloride, styrene, vinyltoluene, acrylonitrile, methacrylonitrile, mono- and di-furmaric or -maleic acid esters, such as of the alkanols having 1 to 4 carbon atoms, including for example, monomethyl fumarate, diethyl maleate or fumarate, dibutyl maleate or monobutyl maleate, or one or two of the acrylic and methacrylic acid esters mentioned above are often used as the film-forming component of aqueous base paints. Similarly, copolymers of one or more of the acrylic or methacrylic acid esters mentioned above with one or more of the following monomers: vinyl acetate, vinyl esters of higher fatty acids, the mono- or di-alkyl esters of itaconic acid, the mono- or di-alkyl esters of fumaric acid or the mono- or di-alkyl esters of maleic acid, such as the esters of methanol, ethanol, or butanol, vinyl chloride, vinylidene chloride, styrene, vinyltoluene, acrylonitrile, and methacrylonitrile are also commonly employed in aqueous base paints. Homopolymers of ethylene or isobutylene, and copolymers of one or more of these hydrocarbons or of styrene with one or more esters, nitriles, or amides of acrylic acid or of methacrylic acid or with vinyl esters, such as vinyl acetate and vinyl chloride, or with vinylidene chloride are also used. The diene polymers are generally used in aqueous base paints in the form of copolymers with one or more monomers following: styrene, vinyltoluene, acrylonitrile, methacrylonitrile, and the above-mentioned esters of acrylic acid or methacrylic acid. It is also quite common to include a small amount, such as about 0.5 to 8% or more, of an acid monomer in the monomer mixture used for making the copolymers of all three general types mentioned above by emulsion polymerization. Acids used include acrylic, methacrylic, itaconic, aconitic, citraconic, crotonic, maleic, fumaric, the dimer of methacrylic acid, and the like.

Particularly useful coating compositions are the copolymers of (a) a soft acrylate, such as a ($C_1$–$C_8$)alkyl acrylate (especially methyl acrylate, ethyl acrylate, butyl acrylate, 2-ethylhexyl acrylate or mixtures thereof), with (b) at least one hard comonomer, such as methyl methacrylate, acrylonitrile, styrene, vinyltoluene, vinyl acetate, and vinyl chloride, and (c) about 0.5 to 8% by weight of an $\alpha\beta$-mono-ethylenically unsaturated acid, such as acrylic, methacrylic, crotonic, or itaconic acid such as those described in Conn et al. U.S. Pat. No. 2,795,564, June 11, 1957; and blends of any of these polymer dispersions with each other or with similar polymers containing a polar group, such as any of the blends mentioned in Scott U.S. Pat. No. 3,356,627, Dec. 5, 1967.

These aqueous dispersions can be made using one or more emulsifiers of anionic, cationic, or nonionic type. Mixtures of two or more emulsifiers regardless of type can be used, except that it is generally undesirable to mix a cationic with an anionic type in any appreciable amounts since they tend to neutralize each other. The amount of emulsifier can range from about 0.1 to 6% by weight or sometimes even more, based on the weight of the total monomer charge. When using a persulfate type or, in general, an ionic type of initiator, the addition of emulsifiers is often unnecessary and this omission or the use of only a small amount e.g. less than about 0.5% of emulsifier, may sometimes be desirable from the cost standpoint (elimination of expensive emulsifier), and less sensitivity of the dried coating or impregnation to moisture, and, hence, less liability of the coated substrate to be affected by moisture, which, for instance, would produce coatings less liable to swelling or softening, particularly when subjected to humid atmospheres. The average particle size or diameter of these dispersed polymers is generally from about 0.03 to 3 microns or even larger.

The compositions of the invention can contain additional materials of various kinds besides the polymeric vehicle to vary the properties and to adapt the compositions for various uses. For example, plasticizers can be added. In making paints, incorporation of pigments and/or dyes is important. The relative proportions of vehicle to pigment may fall in a wide range, such as from a ratio of 1:20 to 20:1 but for most purposes is from 1:5 to 5:1. Pigments can be dispersed in the paint vehicle by any of the well-known techniques of pigment dispersion in paint formulation. In water-based paints, the surfactant for dispersing the pigment composition may be the same or different from the stabilizing surfactants of the polymer vehicle. Ordinarily a concentration of up to 2% of the auxiliary pigment-dispersing surfactant based on the weight of the pigment composition is adequate, the preferred concentration being 0.1% to 1% on the indicated basis. It is preferred that the total amount of pigment dispersing surfactant and the stabilizing surfactants of the respective latices does not exceed 10% based on the total weight of the vehicle.

Water-soluble cellulose derivates such as methyl cellulose, carboxymethyl cellulose or hydroxyethyl cellulose, especially methyl cellulose, can be used for bodying purpose in water-based paints. These materials are used in their ordinary small effective proportions.

Another desirable ancillary component which is preferentially present in aqueous dispersion paint compositions is a volatile water-soluble organic anti-freeze agent to provide the aqueous paint with freeze-thaw stability. Ethylene glycol is especially useful for this purpose at concentrations up to about 5% by weight of the total composition. Other glycols and polyglycols can be used for this purpose.

Aqueous dispersion paint compositions containing surfactants ordinarily foam unless selection of the dispersants is specifically directed to the inherently nonfoaming species. Anti-foam agents can be included in aqueous paint formulations to minimize foaming. High boiling alcohols, polyglycols, silicone liquids and other anti-foam agents well-known to the coating art can be included in the composition as an ancillary component.

For coating compositions which are adequately flexible, external plasticization of the polymer vehicle is ordinarily unnecessary. However, ancillary plasticizer can be included in the compositions in a minor proportion up to 10% by weight of the polymer vehicle, preferably no more than 5%. Non-volitile ester plasticizers, for example, the phosphates, such as tricresyl phosphate, and the phthalates, such as dibutyl phthalate, or the polymeric polyester or alkyd plasticizers can be used.

The total non-volatile content of the coating compositions, ordinarily designated as the solids content, can vary widely. Often, it is desirable that the non-volatile content be at least 30% by weight in order that a practical amount of the film-forming material per coat is applied. The coating compositions often can be satisfactorily formulated in a non-volatile content as great as 70%, but at this concentration thinning may be necessary for satisfactory application. The preferred non-volatile content is from about 40% to 60% by weight.

The viscosity of the coating compositions also can be varied widely. A Stormer viscosity of about 70 to 100 K. U. at 25° C. is a desirable ready-to-apply brush consistency. This is not a critical characteristic as the coating composition can be further modified satisfactorily with thixotropy controlling agents to provide the composition with non-drip characteristics with adequte brushout characteristics.

Other auxiliary materials that may be used include: dispersing agents for dispersing and maintaining in a finely divided state the pigments, colors, or extenders, such as aromatic sulfonates condensed with formaldehyde or any of the suitable commercial dispersing agents such as complex alkali metal phosphates or ethylene polyaminoacetates, defoaming agents, including waxes, oils, or mineral spirits, or an alkylphenoxyethanol, fatty acid amides, phosphate esters, or a solution of an amine or amide in an oil; humectants, such as water-soluble gums, glycol laurate, propylene glycol, diethylene glycol, and the like, thickeners, such as water-soluble gums, water-soluble cellulose ethers, including hydroxyethyl cellulose, water-dispersed starches and proteins, and the like; perfume-like materials, including neutralizing and masking agents, which are used to overcome odors or to impart pleasant and distinctive odors; other resinous materials in dispersed form, such as alkyd resins, drying oils, or latices of styrene or of styrene and butadiene to cheapen and extend the binders of this invention, and auxiliary corrosion-inhibiting agents, such as sodium benzoate, guanyl urea phosphate, or sodium nitrite, in an amount of 0.05% to 5%, and most commonly 0.1% to 2% of the dispersed copolymer, etc.

The compositions of the present invention may be of strictly thermoplastic character or they may be of thermosetting character. The compositions may comprise auxiliary components which impart thermosetting qualities to the composition. For example, there may be added an aldehyde, such as the resin-forming condensates of formaldehyde with phenol, urea, N,N'-ethyleneurea, 5-alkyl- or 5-hydroxyethyl triazones, aminotriazines, such as melamine, as well as the methylated derivatives of these condensates, poly(vic-epoxides) of aliphatic or aromatic types, alkyd resins, that is polyesters of polycarboxylic acids (for example phthalic, adipic, or sebacic) with a polyol (for example ethylene glycol, glycerol, trimethylolethane), and oil-modified types of alkyds containing from 25 to 60% of long chain fatty acid or ester (for example soybean oil). The content of these auxiliary materials may be from 1% to 35% by weight of the total weight of vinyl addition polymeric binder material.

When the thermosetting forms of the compositions of the present invention are used, the coating or impregnation may simply be dried at room temperature or whatever exterior temperature may prevail at the time as would be done with the simple thermoplastic types, reliance for development of cure being placed upon ageing for an extended period of time, for example several days, weeks, or in some cases, months. On the other hand, the cure of such films may be hastened by drying at elevated temperatures or heating at elevated temperatures (up to 200° C.) for several minutes to a half-hour after drying at room temperatures.

Compositions of the present invention can be applied to a wide variety of materials, including textiles, paper, leather, wood, masonry, asbestos-cement shingles or siding, metal, and the like.

For making water-based paints typical formulations generally fall within the scope of the following tabulation which is tabulated on a solids basis:

| Material | Percent by Weight |
|---|---|
| Aqueous dispersed vehicle | 10 to 30 |
| Pigment composition | 1.5 to 55 |
| Stabilizing and dispersing surfactants | 0.1 to 2.5 |
| Bodying or rheology control agent (for example, hydroxyethyl cellulose) | 0 to 2.0 |
| Anti-freeze agent, dry-time extender, and/or solvent (for example, propylene glycol, tributyl phosphate) | 0 to 10.0 |
| Anti-foam agent | 0 to 1.0 |
| Metal compound | 0.025 to 10.0 |
| Preservative (isothiazolone) | 0.02 to 1.0 |
| Ammonium hydroxide (28%), to make a pH of 7.5 to 10 | 0 to 1.5 |
| Water | Balance to make 100 |

The pigment volume concentration is preferably from 18% to 65%. The total of the dispersing and stabilizing surfactants is an amount no greater than 10% based on the weight of water-insoluble material in the binder.

The following examples are set forth to illustrate further this invention but are not intended to limit it in any way:

EXAMPLE 1

The following coating formulation is prepared

Formulation I

| Materials | Pounds per 100 Gallons |
|---|---|
| Hydroxyethylcellulose (2.5% solution) | 85 |
| Water | 62.5 |
| Dispersing Agent (sodium salt of polymethacrylic acid; 30% aqueous solution) | 10.5 |
| Wetting Agent (benzyl ether of tert-octyl phenoxypoly (20) ethoxyethanol) | 2.5 |
| Potassium tripolyphosphate | 1.5 |
| Antifoamer | 1.0 |
| Ethylene Glycol | 25.0 |
| Non-chalking Rutile TiO$_2$ | 237.5 |
| Extender (Talc) | 187.7 |
| Zinc Oxide | 50 |

The above materials are ground in a high speed mill at 3800 to 4500 feet/minute for 20 minutes, and let down, at a slower speed, as follows:

| | |
|---|---|
| Acrylic Vehicle - a 50% solids acrylic dispersion of a copolymer of about 60% ethyl acrylate, about 39% methyl methacrylate, and about 1% methacrylic acid, made by the procedure of Example 1 in U.S. 2,795,564, but unneutralized. | 390.8 |
| Long oil alkyd* | 30.8 |
| Antifoamer | 1.0 |
| Tributyl phosphate } Premix | 9.8 |
| Propylene Glycol } | 35.0 |
| Water | 65.0 |
| Base | Variable |
| Mildeweide - 2-n-octyl-3-isothiazolone/ propylene glycol (1/1 wt. %) | 8.0 |

*Drier treated with 0.5% by weight of 6% cobalt, 0.5% of 6% manganese, and 1.4% of 24% lead, prior to incorporation of alkyd.

After being neutralized with ammonium hydroxide to a pH greater than about 9 and stored at 140° F for 10 days, this formulation shows essentially no chemical decomposition of the isothiazolone. When similar formulations containing no zinc oxide are stored under similar conditions, significant or complete decomposition of the isothiazolone occurs when the formulation has been neutralized to a pH of about 9.5 or higher.

EXAMPLE 2

A coating formulation is prepared in which the acrylic vehicle of Formulation I is replaced with the polyblend acrylic vehicle described in Example 3 of U.S. Pat. No. 3,356,627. This formulation is referred to as Formulation II.

After being neutralized with ammonium hydroxide to different values of pH and stored at 140° F for 10 days, the following degree of decomposition of the isothiazolone (as determined by gas-liquid chromatography) is found:

TABLE I

| Example No. | pH (with NH4OH) | Degree of decomposition[1] without ZnO | with ZnO[2] |
|---|---|---|---|
| 2A | 9.0 | 0 | 0 |
| 2B | 9.5 | 1 | 0 |
| 2C | 9.8 | 3 | 0 |
| 2D | 10.2 | 5 | 0 |
| 2E | 10.4 | 5 | 0 |
| 2F | 10.5 | 5 | 0 |

[1] 0 = essentially no decomposition (less than ~2%); 1 = slight decomposition (up to ~20%); 2 = moderate decomposition (~20 to 40%); 3 = substantial decomposition (~40 to 70%); 4 = severe decomposition (~70 to 100%); 5 = essentially complete decomposition.
[2] 50 pounds of zinc oxide per 100 gallons of paint.

Table I shows the usefulness of zinc oxide in stabilizing an isothiazolone-containing coating formulation against chemical decomposition of the isothiazolone.

EXAMPLE 3

The following coating formulation is prepared:

Formulation III

| Materials | Pounds per 100 Gallons |
|---|---|
| Hydroxyethyl Cellulose (2.5% solution) | 85.0 |
| Water | 68.5 |
| Dispersing Agent (sodium salt of 1:1 mole ratio diisobutylene/maleic anhydride copolymer 25% aqueous solution) | 15.0 |
| Wetting Agent (benzyl ether of tert- | |

Formulation III-continued

| Materials | Pounds per 100 Gallons |
|---|---|
| octyl phenoxypoly (20) ethoxyethanol | 2.5 |
| Antifoamer | 1.0 |
| Ethylene Glycol | 25.0 |
| Non-chalking rutile TiO$_2$ | 250.0 |
| Extender (Talc) | 203.7 |
| Zinc salt* | |

Grind the above materials in a high speed mill (Cowles 3800 to 4500 feet per minute for 10 – 15 minutes) and letdown at slower speed, as follows:

| | |
|---|---|
| Acrylic vehicle - polyblend acrylic of Example 3 of U.S. 3,356,627 (50% solids) | 390.8 |
| Long oil alkyd** | 30.8 |
| Antifoamer | 1.0 |
| Tributyl phosphate } Premix | 9.8 |
| Propylene Glycol } | 35.0 |
| Water and/or hydroxyethylcellulose (2.5%) | 53.5 |
| Base*** | |
| Mildewcide - n-octyl isothiazolone/propylene glycol (1/1 wt. %) | 8.0 |

*Concentration of zinc equivalent to 0.76 pounds of zinc oxide per 100 gallons.
**Drier treated with 0.5% by weight of 6% cobalt, 0.5% of 6% manganese, and 1.4% of 24% lead, prior to incorporation of the alkyd.
***170 millimoles of ammonium hydroxide or dimethylamino-ethanol (DMAE)

After being neutralized with 170 millimoles of ammonium hydrozide or dimethylaminoethanol (DMAE) and stored at 140° F for 5 and 10 days, the following degree of decomposition of the isothiazolone (as determined by gas-liquid chromatography) is found:

TABLE II

| | Degree of Decomposition[1] | | | |
|---|---|---|---|---|
| | NH$_4$OH Neutralized | | DMAE Neutralized | |
| Zinc Salt | 5 days | 10 days | 5 days | 10 days |
| none (control) | 5 | 5 | 4 | 5 |
| zinc chloride | 1 | 5 | — | — |
| zinc acetate | 1 | 5 | — | — |
| zinc oxide | 1 | 5 | — | 1[2] |
| zinc carbonate | 1 | 5 | — | — |
| Zn(NH$_3$)$_2$Cl$_2$ . 2NH$_3$ | 1 | 5 | — | — |

[1] ratings as in Table 1
[2] 50 pounds of zinc oxide per 100 gallons

Table II shows the usefulness of a wide variety of zinc salts in stabilizing an isothiazolone-containing coating formulation against chemical decomposition of the isothiazolone.

EXAMPLE 4

The following coating formulations are prepared:

Formulation IV

The formulation is similar to Formulation I, but as the vehicle has a 50% solids dispersion of copolymer of about 50% butyl methacrylate, about 49% methyl methacrylate, and about 1% methacrylic acid, prepared as described in U.S. Pat. No. 2,795,564.

Formulation V

This formulation is similar to Formulation I, but the polyblend vehicle described in Example 1 of U.S. Pat. No. 3,356,627.

Formulation VI

This formulation is similar to Formulation I, but has the polyblend vehicle described in Example 7(a) of U.S. Pat. No. 3,356,627.

Formulation VII

This information is similar to Formulation I, but has as the vehicle a 50% solids dispersion of the polymer described in Example 4 of U.S. Pat. No. 2,795,564.

In the above formulations, when a zinc salt is present, the formulation is stabilized against chemical decomposition of the 3-isothiazolone. However, when the zinc salt is absent, significant decomposition of the isothiazolone occurs on prolonged storage.

EXAMPLE 5

Formulations are prepared in which the isothiazolone of Formulation I is replaced by:
a. 2-n-hexyl-3-isothiazolone
b. 2-t-butyl-3-isothiazolone
c. 5-chloro-2-n-octyl-3-isothiazolone
d. 2-(3,4-dichlorobenzyl)-3-isothiazolone
e. 2-(p-chlorophenylethyl)-3-isothiazolone
f. 3-isothiazolone
g. 2-n-decyl-3-isothiazolone
h. 2-benzyl-3-isothiazolone In the above formulations, when a zinc compound is present in the formulation, the formulation is stabilized against decomposition of the isothiazolone. However, when the zinc compound is absent, decomposition of the isothiazolone occurs on storage.

EXAMPLE 6

Formulations ae prepared in which the zinc compound of Formulation I is replaced by a compound of cadmium, chromium, cobalt, copper, lead, manganese, mercury and silver. These formulations are stabilized against chemical decomposition of the isothiazolone.

EXAMPLE 7

This example shows the mildew resistance of coatings made from the compositions of the invention. Test panels (white pine) are painted with two coats of the composition of Formulation III, containing varying amounts of zinc oxide and 2-n-octyl-3-isothiazolone. After 9 months of exposure (Florida, South 45°), mildew control is evaluated. The results of these tests are summarized in Table III.

TABLE III

| Zinc Oxide (lbs/100 gal) | Isothiazolone (lbs/100 gal) | Mildew Rating |
|---|---|---|
| 0 | 0 | moderate to very heavy |
| 0 | 1 | moderate |
| 0 | 2 | moderate to heavy |
| 0 | 4 | slight to moderate |
| 0 | 6 | slight |
| 50 | 0 | slight to moderate |
| 50 | 0.5 | very slight to slight |
| 50 | 1 | slight |

TABLE III-continued

| Zinc Oxide (lbs/100 gal) | Isothiazolone (lbs/100 gal) | Mildew Rating |
|---|---|---|
| 50 | 2 | trace |
| 50 | 4 | trace |

It is believed that the zinc oxide and the isothiazolone may function in the coating in a synergistic fashion to improve greatly the mildew resistance of the coating. The data of Table III shows the improvement in mildew resistance obtained in coating compositions containing both an isothiazolone and zinc oxide.

Results of accelerated heat aging tests are shown in Table IV. It can be seen that compounds of zinc, molybdenum, copper (cuprous, cupric), lead, and mercury effectively prevent isothiazolone decomposition, even at a level of 5 lbs/100 gal., as evidenced by the lack of any appreciable depreciation in active ingredient. None of the remaining compounds listed demonstrate any discernible stabilizing effect.

TABLE IV 2-n-octyl-4-isothiazolin-3-one
Chemical Stability Data

| Metal Compound[a] | Formula | % Active ingredient[c] Remaining after 10 days/140° F[d] | |
|---|---|---|---|
| | | 5 lb.[e] | 50 lb.[e] |
| Zinc Oxide | ZnO | 94 | 100 |
| Molybdenum Oxide | MoO$_3$ | 95[h] | i |
| Cuprous Oxide | Cu$_2$O | 100 | i |
| Cupric Oxide | CuO | 95 | — |
| Lead Silicate[b] | PbSiO$_3$ | 94 | 94 |
| Di-(Phenyl mercury) dodecenyl succinate | (OH$_a$)$_2$R$^g$ | 100 | — |
| Calcium Carbonate | CaCO$_3$ | 0 | 0 |
| Barium Sulfate | BaSO$_4$ | 0 | 0 |
| Cerium Oxide | CeO$_2$ | 0 | 0 |
| Ferric Oxide | Fe$_2$O$_3$ | 0 | 0 |
| Chromium Oxide | Cr$_2$O$_3$ | 0 | 0 |
| Stannic Oxide | SnO$_2$ | 0 | 0 |
| Antimony Oxide | Sb$_2$O$_3$ | 0 | i |
| None added (control) | — | | 0 |

[a]Incorporated into formulation Type A paints containing 2 lb. isothiazolone per 100 gallons of paint.
[b]Purity 95% unless otherwise noted.
[c]Active ingredient is (2-n-octyl-4-isothiazolin-3-one)
[d]Determined by GLC analysis estimated accuracy +10%.
[e]Level of metal compound per 100 gallons of paint, except as noted.
[f]Basic lead silicate, pigment grade of complex composition.
[g]Used at a 5 lb. level as supplied (solvent solution of 21% di(phenyl mercury) dodecenyl succinate containing 10% mercury metal) (sold under trademark Super-Ad-It)
[h]Stabilization probably due to pH reduction caused by reaction of MoO$_3$ with base.
[i]Paint unstable.

The remaining metal compounds listed in Table IV show no stabilizing effect on isothiazolone even at a level of 50 lbs./100 gals. This is attributed to their inability to produce stable sulfides under basic conditions.

TABLE V

| Materials | Test Formulation A | |
|---|---|---|
| | lbs./100 gal. | |
| Hydroxyethyl Cellulose (2.5% sol.) | 85.0 | 85.0 |
| Water | 62.5 | 62.5 |
| Dispersing Agent (Sodium salt of 1:1 mole ratio diisobutylene/maleic anhydride copolymer 25% aqueous solution | 10.5 | 10.5 |
| Wetting Agent (Benzyl ether of tert-octyl phenoxypoly (20) ethoxyethanol | 2.5 | 2.5 |
| Potassium tripolyphosphate | 1.5 | 1.5 |
| Antifoamer | 1.0 | 1.0 |
| Ethylene Glycol | 25.0 | 25.0 |
| Non-chalking Rutile TiO$_2$ | 250.0 | 250.0 |
| Talc Extender | 200.00 | 157.0 |
| Metal Compound | 5.0 | — |

TABLE V-continued

| Materials | Test Formulation A | lbs./100 gal. |
|---|---|---|
| Metal Compound | — | 50.0 |
| Grind the above on a high speed mill for 12–15 minutes at 3800–4500 feet/minute then let down at a slower speed as follows: | | |
| Acrylic vehicle (polyblend acrylic of Example 3 of U.S. 3,356,627) (50% solid) | 390.8 | 390.8 |
| Long Oil Alkyd[1] | 30.0 | 30.8 |
| Tributyl Phosphate | 9.8 | 9.8 |
| Propylene Glycol | 35.0 | 35.0 |
| (45% n-octyl isothiazolone) premix | 2.0 | 2.0 |
| Ammonium Hydroxide (28%) | 3.0 | 3.0 |
| Antifoamer | 1.0 | 1.0 |
| Water and/or hydroxyethyl cellulose (2.5%) | 65.0 | 65.0 |

[1]Drier treated with 0.5% by weight of 6% Cobalt, 0.5% of 6% manganese and 1.4% of 24% zirconium.

The following explanation is provided to enable one skilled in the art to better understand the operation of this invention. This explanation is presented merely as an illustration of the present invention and is not to be considered as a limitation in anyway of the scope of this invention.

In studies concerning the chemical stability of isothiazolones in latex paints it was established that ammonia, not hydroxide ion per se, is largely responsible for the decomposition which occurs under basic pH conditions (i.e. 9.0 to 10.0). The mechanism of isothiazolone decomposition is envisioned as one involving initial ring opening (at the S—N bond) by the nucleophilic attack of ammonia at the sulfur position. This reaction is considered to be relatively slow, although it is much faster than that involving hydroxide ion in paint. However, the products of the ring-opening further degrade to produce sulfide ion as evidenced by H₂S odor produced. The sulfide ion in turn greatly increases the overall rate of ring opening because of its greater nucleophilicity as compared to ammonia. Accordingly, the decomposition reaction becomes essentially autocatalytic.

Thus it is seen that various metal compounds are exceedingly effective in stabilizing isothiazolones against chemical degradation. Such a use of metal compounds to stabilize isothiazolones in aqueous dispersions of vinyl or acrylic emulsion polymer coating compositions is an essential part of this invention particularly at pH values greater than 9.0. However it is to be understood that changes and variations of this stabilization concept may be made without departing from the spirit and scope of the invention as defined by the appended claims.

We claim:

1. A coating composition which comprises an aqueous dispersion of a vinyl or acrylic emulsion polymer having a pH greater than 9.0, a mildew-controlling amount of an isothiazolone of the formula

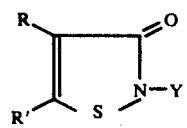

wherein Y is a hydrogen atom, a ($C_1$–$C_{18}$) alkyl group, a ($C_6$–$C_{10}$) aryl group, or a ($C_7$–$C_{10}$) aralkyl group;
R is a hydrogen atom, a halogen atom, or a ($C_1$–$C_4$) alkyl group,
R' is a hydrogen atom, a halogen atom, or a ($C_1$–$C_4$) alkyl group, or
R and R' can be taken together to complete a benzene ring, optionally substituted with one or more halogen atoms, nitro groups, ($C_1$–$C_4$) alkyl groups, cyano groups, or ($C_1$–$C_4$) alkoxy groups, and a stabilizing amount of a metallic compound of zinc, molybdenum, copper (cuprous, cupric), lead or mercury.

2. The composition of claim 1 wherein the metallic compound is zinc oxide, molybdenum oxide, cuprous oxide, cupric oxide, lead silicate or di-(phenylmercury) dodecenyl succinate.

3. The composition of claim 2 wherein Y is a ($C_1$–$C_{18}$) alkyl group.

4. The composition of claim 3 wherein R and R' are hydrogen atoms and the metallic compound is a zinc compound.

5. The composition of claim 4 wherein the isothiazone is 2-n-octyl-4-isothiazolin-3-one.

6. The composition of claim 5 wherein the metallic compound is zinc oxide.

7. The composition of claim 2 wherein the emulsion polymer is an acrylic emulsion polymer.

8. The composition of claim 2 which additionally comprises a pigment.

9. The composition of claim 3 wherein the metallic compound is present in an amount of about 0.01 to about 100 pounds per 100 gallons of the composition.

10. The composition of claim 3 wherein the isothiazolone is present in an amount of about 0.5 to about 12 pounds per 100 gallons of the composition.

11. A method of stabilizing an isothiazolone containing coating composition having a pH greater than 9.0 which comprises, incorporating into the composition a stabilizing amount of a metallic compound of zinc, molybdenum, copper (cuprous, cupric), lead or mercury, and mixtures thereof.

12. The method of claim 11 wherein the metallic compound is zinc oxide.

13. A method of controlling mildew in a solid coating which comprises incorporating into the coating composition, a mildew-controlling amount of an isothiazolone of the formula:

wherein Y is a hydrogen atom, a ($C_1$–$C_{18}$) alkyl group, a ($C_6$–$C_{10}$) aryl group, or a ($C_7$–$C_{10}$) aralkyl group;
R is a hydrogen atom, a halogen atom, or a ($C_1$–$C_4$) ($C_1$–$C_4$) alkyl group,
R' is a hydrogen atom, a halogen atom, or a ($C_1$–$C_4$) alkyl group, or
R and R' can be taken together to complete a benzene ring, optionally substituted with one or more halogen atoms, nitro groups, ($C_1$–$C_4$) alkyl groups, cyano groups, or ($C_1$–$C_4$) alkoxy groups, and a stabilizing amount of a metallic compound of zinc, molybdenum, copper (cuprous, cupric) lead or mercury.

14. The method of claim 13 wherein the metallic compound is zinc oxide.

* * * * *